US010703692B2

(12) United States Patent
Pitman et al.

(10) Patent No.: US 10,703,692 B2
(45) Date of Patent: Jul. 7, 2020

(54) SOLID STATE MATERIALS WITH TUNABLE DIELECTRIC RESPONSE AND ROTATIONAL ANISOTROPY

(71) Applicant: RAYTHEON COMPANY, Waltham, MA (US)

(72) Inventors: Michael Pitman, Tucson, AZ (US); Teresa J. Clement, Tucson, AZ (US); Glafkos K. Stratis, Tucson, AZ (US); Alphonso A. Samuel, Tucson, AZ (US); Alex Dely, Tucson, AZ (US); Wayne L. Sunne, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 253 days.

(21) Appl. No.: 15/425,101

(22) Filed: Feb. 6, 2017

(65) Prior Publication Data
US 2018/0222826 A1    Aug. 9, 2018

(51) Int. Cl.
C07C 15/60     (2006.01)
H01L 51/05     (2006.01)
H01L 51/00     (2006.01)
G02F 1/00      (2006.01)
H01Q 15/00     (2006.01)
C07F 9/12      (2006.01)
C07C 255/34    (2006.01)

(52) U.S. Cl.
CPC ............ C07C 15/60 (2013.01); C07C 255/34 (2013.01); C07F 9/12 (2013.01); G02F 1/0054 (2013.01); G02F 1/0081 (2013.01); H01L 51/0595 (2013.01); H01Q 15/0006 (2013.01); G02F 1/009 (2013.01); G02F 2202/30 (2013.01); H01L 51/0052 (2013.01)

(58) Field of Classification Search
CPC ..... C07C 15/28; C07C 15/60; H01L 51/0595; H01L 51/0052
USPC .......................................................... 257/40
See application file for complete search history.

(56) References Cited

U.S. PATENT DOCUMENTS

| | | | | |
|---|---|---|---|---|
| 3,911,038 | A | | 10/1975 | Maulding |
| 4,235,996 | A | * | 11/1980 | Child ........................ C07C 17/32 544/296 |
| 4,258,181 | A | * | 3/1981 | Murdock ................ C07C 17/32 540/467 |
| 4,405,513 | A | * | 9/1983 | Kamhi ..................... C09K 11/07 252/186.43 |
| 4,547,317 | A | | 10/1985 | Kamhi |
| 6,430,511 | B1 | * | 8/2002 | Tour ....................... B82Y 10/00 435/6.11 |
| 6,795,230 | B1 | * | 9/2004 | Vincent .................... B82Y 30/00 359/321 |
| 8,178,873 | B2 | * | 5/2012 | Zhu ....................... H01L 51/0052 257/40 |
| 2008/0269486 | A1 | * | 10/2008 | Zhou ..................... B82Y 10/00 544/250 |
| 2008/0309864 | A1 | * | 12/2008 | Lee ........................ C09K 19/32 349/139 |
| 2009/0286065 | A1 | * | 11/2009 | Bonifazi ................... B82B 3/00 428/315.5 |
| 2010/0270542 | A1 | * | 10/2010 | Zhu ..................... H01L 51/0052 257/40 |
| 2012/0128878 | A1 | * | 5/2012 | Li .......................... B82Y 30/00 427/215 |
| 2014/0081014 | A1 | * | 3/2014 | Yaghi .................... C07D 487/22 540/145 |
| 2014/0221655 | A1 | * | 8/2014 | Strauss .................. C07C 17/32 546/88 |
| 2016/0079536 | A1 | * | 3/2016 | Diez .................... H01L 51/0012 257/40 |
| 2016/0259256 | A1 | * | 9/2016 | Cote ..................... G03G 5/0539 |
| 2017/0301477 | A1 | * | 10/2017 | Lazarev ................. C08F 20/36 |
| 2018/0222825 | A1 | * | 8/2018 | Pitman ................... C07C 13/62 |

FOREIGN PATENT DOCUMENTS

| | | | | |
|---|---|---|---|---|
| EP | 3115392 | A1 * | 1/2017 | ................ C08J 5/18 |
| WO | 2012127542 | A1 | 9/2012 | |
| WO | WO-2017002643 | A1 * | 1/2017 | ......... H01L 51/0073 |

(Continued)

OTHER PUBLICATIONS

Zhu et al. Applied Physics Letters 99, 221102 (Year: 2011).*
Zheng et al. Journal of Materials Chemistry C, Issue 10:2, pp. 1913-1920 (Year: 2014).*
Zhang et al. Applied Physics Letters 111, 241106 (Year: 2017).*
Notification of Transmittal of The International Search Report and The Written Opinion of The International Searching Authority, or The Declaration; International Application No. PCT/US2018/016614; International Filing Date Feb. 2, 2018; dated Jul. 16, 2018; 7 pages.

(Continued)

Primary Examiner — Joseph R Kosack
(74) Attorney, Agent, or Firm — Cantor Colburn LLP

(57) ABSTRACT

A reconfigurable polar molecule includes a symmetric nonpolar molecule portion having an elongated shape defined by a longitudinal axis and lateral axis, the longitudinal axis being longer than the lateral axis; a positive ionically charged group at a first end and a negative ionically charged group at a second end of the longitudinal axis, the positive and negative ionically charged groups forming a permanent dipole; a first bridging group and a second bridging group on opposing ends of the lateral axis, the first and second bridging groups being linear nonpolar groups; and a first support portion bonded to the first bridging group, and a second support portion bonded to the second bridging group, the first bridging group and the second bridging group being nonpolar and having structures that enable free rotation of the symmetric nonpolar molecule portion through the first bridging group and the second bridging group.

12 Claims, 4 Drawing Sheets

(56) References Cited

FOREIGN PATENT DOCUMENTS

WO    WO-2017046554 A1 * 3/2017 ........... C07D 495/04

OTHER PUBLICATIONS

Written Opinion of the International Searching Authority; International Application No. PCT/US2018/016614; International Filing Date Feb. 2, 2018; Priority Date Jun. 2, 2017; dated Jul. 16, 2018; 12 pages.
A. Andre et al., "Hybrid Quantum Information Processing with Polar Molecules," American Institute of Physics, 2006, pp. 128-135.
Stratis, et al. "Electric Field Dependence of the Competition Between Permanent and Induced Dipole Orientation in Suspensions of Large Anisotropic Particles," Electromagnetics, 1991, vol. 11, pp. 309-323.

* cited by examiner

SOLID STATE MATERIALS WITH TUNABLE DIELECTRIC RESPONSE AND ROTATIONAL ANISOTROPY

BACKGROUND

The present invention relates to tunable and reconfigurable molecules and materials, and more specifically, to tunable and reconfigurable solid state molecules and materials.

A tunable metamaterial could be a material with a variable response to an incident electromagnetic (EM) wave (such as a radio frequency (RF) wave or an optical frequency wave). A tunable metamaterial also could be a material arranged in a relationship with a local applied voltage, externally applied heat, plasma, chemical reactions, and the like. The foregoing are various physical properties that can be used in certain combinations to form a tunable material. For example, remote control of an EM wave may be used to regulate how an incident EM wave interacts with a metamaterial; such remote control can also be combined with a local voltage or any one of the physical entities mentioned above.

Tunable metamaterials include a lattice structure of unit cells. The lattice structure of the tunable metamaterial is adjustable in real time, which makes it possible to reconfigure during operation. Reconfigurable and tunable materials may be used in various applications, including RF and infrared (IR) applications, quantum computing/cryptography/optics, and even spintronics. More specifically, a polar molecule can behave as a reconfigurable material. The rotation of the polarity (of the polar molecule) can induce separation of polarization states of light or separation of electrons with different spins.

Polar molecules can be in the liquid state (liquid polar molecules) or in the solid state (solid state polar molecules). In the case of both liquid polar molecules and solid state polar molecules, the polar molecule interacts with a local potential (voltage), or the polar molecule may be aligned with the polarization of the incident EM wave. This alignment can be combined with feedback control in a dynamic manner, which is why adaptive rotational anisotropy is achieved. The liquid polar molecule still has the symmetry of an ellipsoid, but in addition, it has positive and negative charges (local charges) along that ellipsoid symmetry. Thus, the distinction, between the neutral ellipsoid in liquid crystals and the polar molecule ellipsoid, is the local potential that causes the interactions with external fields and therefore causes rotation of the polar molecule and therefore the anisotropy.

Anisotropy is when the dielectric, magnetic, and/or thermal properties of a material are different in different directions. In an isotropic material, the electric, magnetic, and thermal properties are the same in all directions. For example, the transmissivity or reflectivity of an isotropic material is the same in any direction. In an anisotropic material, the transmissivity (of an EM field, for example) or reflectivity is different in different directions, which means that the reflection and transmission coefficients are different in different directions, inside the material. In another example, heat flow is different in all directions in anisotropic materials, whereas heat flow in isotropic materials is the same in all directions. In the foregoing examples, the properties are fixed.

Rotational anisotropy means that the dielectric, magnetic, and/or thermal properties of the material depend on the orientation of the anisotropy, which is rotational. In such a case, the reflection and/or transmission coefficients are also rotational. Accordingly, the polar molecule dynamically rotates, which occurs through interactions with a control voltage, local or incident voltage, or both. Rotational anisotropy can be controlled with external potentials or feedback controls in a dynamic or adaptive manner; this is why the polar molecules (liquid and solid) have advantages in some specific applications compared to the neutral ellipsoid in liquid crystal structures. Embodiments of the invention described in detail below are focused on the solid state polar molecule, which exhibits rotational anisotropy, and in many cases rotational anisotropy in an adoptive manner. Furthermore, other embodiments described in further detail below, relate to the overall design of the solid rotational polar molecule, which has advantages over liquid polar molecules.

SUMMARY

According to an embodiment, a reconfigurable polar molecule includes a symmetric nonpolar molecule portion having an elongated shape and defined by a longitudinal axis and a lateral axis, the longitudinal axis being longer than the lateral axis; a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule; a first bridging group and a second bridging group arranged on the lateral axis of the symmetric nonpolar molecule on opposing sides, the first bridging group and the second bridging group being linear nonpolar groups; and a first support portion bonded to the first bridging group, and a second support portion bonded to the second bridging group, the first bridging group and the second bridging group being nonpolar and having structures that enable free rotation of the symmetric nonpolar molecule portion through the first bridging group and the second bridging group.

According to another embodiment, a reconfigurable polar molecule includes a symmetric nonpolar molecule portion having an elongated shape, including a polyaromatic ring structure, and defined by a longitudinal axis and a lateral axis, the longitudinal axis being longer than the lateral axis; a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule; a first bridging group and a second bridging group arranged on the lateral axis of the symmetric nonpolar molecule on opposing sides, the first bridging group and the second bridging group being linear nonpolar groups; an axis of rotation extending from the first bridging group to the second bridging group along the lateral axis of the symmetric nonpolar molecule; and a first nonpolar support portion bonded to the first bridging group on one side of the symmetric nonpolar molecule, and a second nonpolar support portion bonded to the second bridging group on an opposing side of the symmetric nonpolar molecule, the first bridging group and the second bridging group being nonpolar and having structures that enable free rotation of the symmetric nonpolar molecule portion through the first bridging group and the second bridging group.

Yet, according to another embodiment, a method of using a reconfigurable polar molecule includes forming the reconfigurable polar molecule, including: a symmetric nonpolar molecule portion having an elongated shape and defined by a longitudinal axis and a lateral axis, the longitudinal axis being longer than the lateral axis; a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule; a first bridging group and a second bridging group arranged on the lateral axis of the symmetric nonpolar molecule at opposing sides, the first bridging group and the second bridging group being linear nonpolar groups; and a first support portion bonded to the first bridging group, and a second support portion bonded to the second bridging group, the first bridging group and the second bridging group being nonpolar and having structures that enable free rotation of the symmetric nonpolar molecule portion through the first bridging group and the second bridging group with respect to the first support portion and the second support portion; and applying an electric field to the reconfigurable polar molecule to induce the reconfigurable polar molecule to rotate through an axis of rotation that extends through the lateral axis of the symmetric nonpolar support molecule.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIGS. 1-4B illustrate exemplary reconfigurable polar molecules and solid state materials according to embodiments, in which:

FIG. 1 illustrates system components of a reconfigurable polar molecule;

FIG. 2 illustrates illustrates the tunable EM response of a solid state reconfigurable polar molecule;

FIG. 3 illustrates a solid state material having individual molecules arranged in a lattice;

FIG. 4B is a primary rotating element anchored within a packaging architecture.

DETAILED DESCRIPTION

Because of their polar nature and rotational anisotropy, liquid polar materials may be used in a variety of RF and IR applications, quantum computers, and/or optics applications. However, liquid crystals may have limited capabilities. For example, liquid crystals may only be operational within a narrow temperature range. Liquid crystals also may be more sensitive to EM fields under certain circumstances or conditions, for example, if the EM (time varying field) field is too strong, the rotational motion of the polar molecule is not sustained. This causes translational motion instead of rotation, which is the desired motion in this case. Under some circumstances, due to their liquid state, liquid crystals may also become inherently disordered (or lose their alignment).

Accordingly, various embodiments described herein provide reconfigurable polar molecules with controllable rotational anisotropy. The individual molecules (or systems) are ordered in a three-dimensional lattice to form solid state materials with improved thermal stability relative to liquid crystals. The reconfigurable polar molecules are substantially rigid and have a permanent dipole, with the exception of a designed internal degree of freedom to allow for rotation in the solid state. Another advantage of the inventive solid state polar molecules, compared to liquid state polar molecules, is the solid state nature makes its reaction occur at a much faster rate than liquid polar molecules, which have a slower response due to their liquid nature. The reconfigurable anisotropy can be controlled by external or local EM fields governed by algorithms. The molecules also have a rotational axis through its center of mass. The molecules are packaged within a supporting architecture that ensures an unobstructed path for rotation. The sizes of the polar molecules are selected to facilitate RF, IR, or other applications mentioned above.

As used herein, the term "reconfigurable" when used in reference to a molecule means rotating in response to an applied external electric field.

As used herein, the term "polar" when used in reference to a molecule means having a net dipole as a result of partial negative and positive charges due to asymmetrically arranged polar bonds.

As used herein, the term "nonpolar" when used in reference to a molecule means having no net dipole (or charge) due to equal sharing of electrons between atoms in the molecule.

Figure 1:
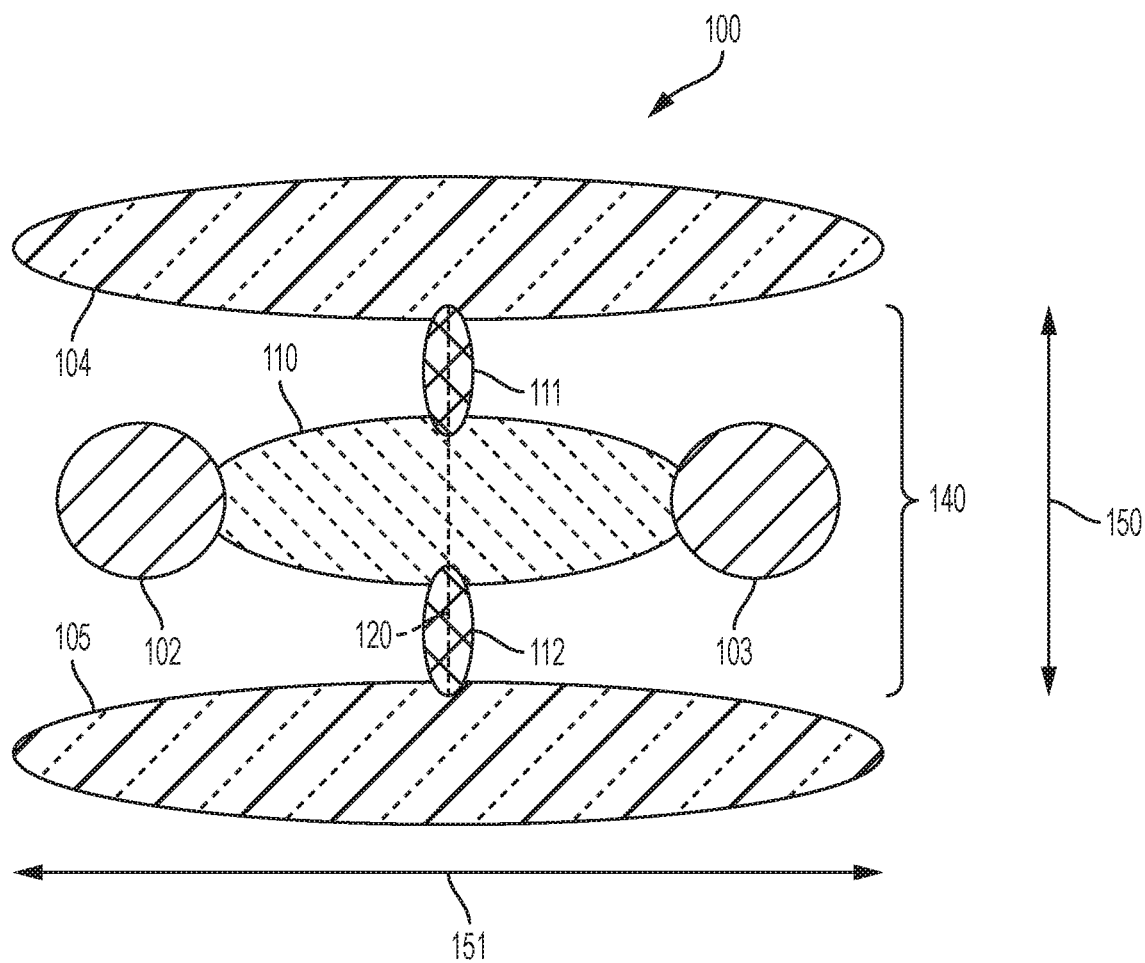

Turning now to the Figures, FIGS. 1-4B illustrate molecular system components and solid state materials according to embodiments. FIG. 1 illustrates system components of a reconfigurable polar molecule 100. The primary rotating element 140 of the reconfigurable polar molecule 100 includes an elongated segment 110 having a first charged end 102 and a second charged end 103. Elongated segment 110 is substantially rigid, symmetric, and nonpolar. The elongated segment 110 provides a rigid scaffold that does not bend or twist. The elongated segment 110 has an elongated shape, or an elliptical shape, in some embodiments. The elongated segment 110 is defined by a long longitudinal axis and a shorter lateral axis.

First charged end 102 and second charged end 103 are arranged on the longitudinal axis of elongated segment 110. First charged end 102 and second charged end 103 are arranged on opposing ends of elongated segment 110 and form a permanent dipole through the longitudinal axis. First charged end 102 is a permanent positive ionic charge, or cation. Second charged end 103 is a permanent negative ionic charge, or an anion or a stable negative charge in the environment. For example first changed end 102 and second charged end 103 could represent a zwitterionic state. First charged end 102 and second charged end 103 are not induced dipoles. First charged end 102 and second charged end 103 are permanent ionic charges. First charged end 102 and second charged end 103 are permanent ionic charges that are opposite charges. In one example, first charged end 102 is a permanent positive charge, or cation, and second charged end 103 is a permanent negative charge, or anion. In another example, first charged end 102 is a permanent negative charge, and second charged end 103 is a permanent positive charge.

Although first charged end 102 and second charged end 103 are shown as being arranged on distal ends of elongated segment 110, first charged end 102 and second charged end 103 do not have to be specifically positioned on the far distal ends of elongated segment 110. In other words, the ionic charge of the first charged end 102 and second charged end 103 may be formed from a group that includes other atoms or groups such that the other atoms or groups are arranged on the distal ends. The rigid scaffold of elongated segment 110 ensure that first charged end 102 and second charged end 103 do not collapse onto one another.

As mentioned above, elongated segment 110 has an elliptical shape. Elongated segment 110 may include hydrocarbon systems with aromatic rings, planar fused rings, and/or planar heterocyclic molecules. Suitable hydrocarbon systems may include one or more aromatic rings (polyaromatic ring structures), one or more conjugated ring structures, one or more substituted aromatic rings, one or more saturated hydrocarbons, one or more unsaturated hydrocarbons, one or more substituted hydrocarbons, or any combination thereof. Elongated segment 110 may include substitutions on the hydrocarbon systems, provided that the substitutions result in a nonpolar molecule.

In one exemplary embodiment, elongated segment 110 is an anthracene derivative having the following structure (structure I):

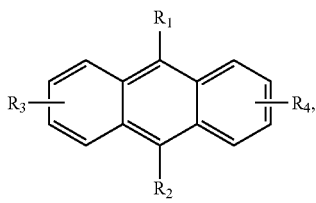

Where in $R_1$ and $R_2$ are each an ethynyl group; $R_3$ is a positively charged ionic group; and $R_4$ is a negatively charged ionic group.

Elongated segment 110 is not limited to organic hydrocarbon systems. In some embodiments, elongated segment 110 may include other nanoparticles, including, but not limited to, helices, carbon nanotubes, or combinations thereof. However, regardless of the composition, elongated segment 110 should remain substantially symmetric and nonpolar so that, as discussed below, primary rotating segment 140 may freely rotate.

Elongated segment 110 is derivatized at each end on the longitudinal axis to form first charged end 102 and second charged end 103. First charged end 102 and second charged end 103 may include any positive charged ionic group or any negatively charged ionic group. Non-limiting examples of positively charged ionic groups include positively charged amine groups, ammonium groups, phosphonium groups, sulfonium group, salts thereof, or any combination thereof. Non-limiting examples of negatively charged ionic groups include carboxylate groups, phosphate groups, phosphonate groups, sulfate groups, sulfonates groups, nitrate groups, nitrite groups, tosylate groups, brosylate groups, mesylate groups, selenate groups, salts thereof, or any combination thereof.

Elongated segment 110 is connected to a first support 104 by a first bridging group 111. Elongated segment 110 is connected to a second support 105 by a second bridging group 112. First bridging group 111 and second bridging group 112 are each connected to first support 104 and second support 105, respectively, by one or more interactions or bonds. First bridging group 111 and second bridging group 112 are arranged at opposing sides of elongated segment 110 on the shorter lateral axis of elongated segment 110 and along the axis of rotation 120. First bridging group 111 and second bridging group 112 are also arranged substantially perpendicular to the permanent dipole formed on the longitudinal axis of elongated segment 110. As described below, first bridging group 111 and second bridging group 112 allow free rotation of elongated segment 110 with respect to first support 104 and second support 105, respectively.

The interactions and/or bonds between first bridging group 111 and first support 104 and second bridging group 112 and second support 105 depend on the identities of the constituent groups. The interactions and/or bonds between first bridging group 111 and first support 104 and second bridging group 112 and second support 105 include, for example, covalent bonds, hydrogen bonds, electrostatic interactions, hydrophobic interactions, metal complexation interactions, or any combination thereof.

First bridging group 111 and second bridging group 112 may be linear, nonpolar hydrocarbon groups. First bridging group 111 and second bridging group 112 may be the same or different. First bridging group 111 and second bridging group 112 anchor elongated segment 110 on axis of rotation 120 and provide a low barrier to free rotation (described below in FIG. 2). The axis of rotation 120 extends through the center of mass of primary rotating element 140. Each of first bridging group 111 and second bridging group 112 may be, for example, a linear hydrocarbon group, such as an alkynyl group, or an alkynyl-containing group. In one example, first bridging group 111 and second bridging group 112 are each linear ethynyl groups or linear cyano groups. First bridging group 111 and second bridging group 112 may form carbon-carbon covalent bonds with first support 104 and second support 105, respectively.

Elongated segment 110 can freely rotate under the influence of an externally stimulus of appropriate magnitude and orientation, as described in further detail below with reference to FIG. 2. For example, under the influence of an externally applied electric field, elongated segment 110 rotates along the axis of rotation 120. The permanent dipole of elongated segment 110 is directed approximately perpendicular to first bridging group 111 and approximately perpendicular to second bridging group 112.

First support 104 and second support 105 may be any nonpolar support structures or moieties. First support 104 and second support 105 should provide an unobstructed path for rotation about the axis of rotation 120. First support 104 and second support 105 thus provide the material housing (packaging) around the rotational path (axis of rotation 120) of primary rotating element 140, which allows for full rotation in response to applied electric fields. The material housing forming first support 104 and second support 105 may be the same or different. The material housing forming first support 104 and second support 105 insulates primary rotating element 140 from dispersion and ambient vibrational modes. The shape of the packaging forming first support 104 and second support 105 governs three-dimensional (3D) assembly into solid state 3D materials.

The materials and composition of the first support 104 and second support 105 may generally vary and depend on the desired properties of the solid state material and particular application. The first support 104 and second support 105 each include nonpolar molecules. The size and shape of each of the first support 104 and second support 105 may generally vary and depend on the type of solid state material desired, as such properties govern the three-dimensional assembly into the solid state material.

The first support 104 and second support 105 may include a low-k dielectric material. For example, first support 104 and second support 105 materials may have a dielectric constant, or k-value, in a range from about 2 to about 8, ideally with zero loss tangent. In one embodiment, first support 104 and second support 105 include polyaromatic ring structure-containing walls that minimize dispersion.

In an exemplary embodiment, solid state reconfigurable polar molecule 100 has the following structure (structure II):

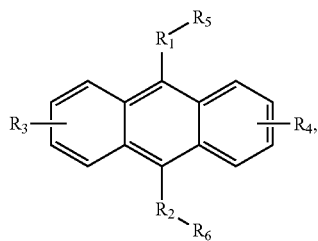

wherein $R_1$ and $R_2$ are each independently a $C_2$-$C_4$ alkyl group, a $C_2$-$C_4$ alkenyl group, a $C_2$-$C_4$ alkynyl group, a cyano group, or any combination thereof; $R_3$ is a positively charged ionic group; $R_4$ is a negatively charged ionic group; and $R_5$ and $R_6$ are each independently an non-polar support moiety. The $C_2$-$C_4$ alkyl group, $C_2$-$C_4$ alkenyl group, and $C_2$-$C_4$ alkynyl group may be branched, unbranched, substituted, or unsubstituted.

In another embodiment, solid state reconfigurable polar molecule 100 has the following structure (structure III):

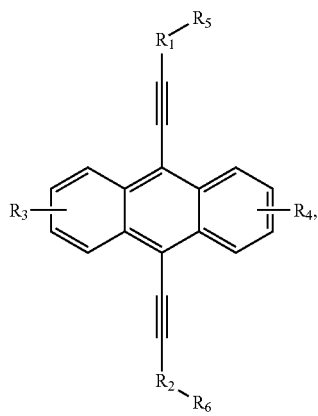

wherein $R_1$ and $R_2$ are each independently a single bond, a $C_2$-$C_4$ alkyl group, a $C_2$-$C_4$ alkenyl group, a $C_2$-$C_4$ alkynyl group, a cyano group, or any combination thereof; $R_3$ is a positively charged ionic group; $R_4$ is a negatively charged ionic group; and $R_5$ and $R_6$ are each independently an non-polar support moiety. The $C_2$-$C_x$ alkyl group, $C_2$-$C_x$ alkenyl group, and $C_2$-$C_x$ alkynyl group may be branched, unbranched, substituted, or unsubstituted.

When solid state reconfigurable polar molecule 100 includes an alkynyl group, as shown in structure III above, the axis of rotation 120 (shown in FIG. 1) extends through the alkynyl group and is arranged substantially perpendicular to the permanent dipole formed on elongated segment 110 from first charged end 102 and second charged end 103 on the long longitudinal axis.

Dimensions of the solid state reconfigurable polar molecule 100 depend on dimensions of the packaging (first support 104 and second support 105) and primary rotating element 140. The primary rotating element 140 has nanometer-scale dimensions. In one embodiment, primary rotating element 140 has a length 151 in a range from about 1 to about 2 nanometers (nm). The dimensions of the primary rotating element 140 and packaging (first support 104 and second support 105) can be selected to facilitate both RF and IR optical applications. Assemblies of the basic units can be tuned to larger wavelengths (RF); this is analogous to alignment of small compasses in an EM field in the RF regimes.

Figure 2:
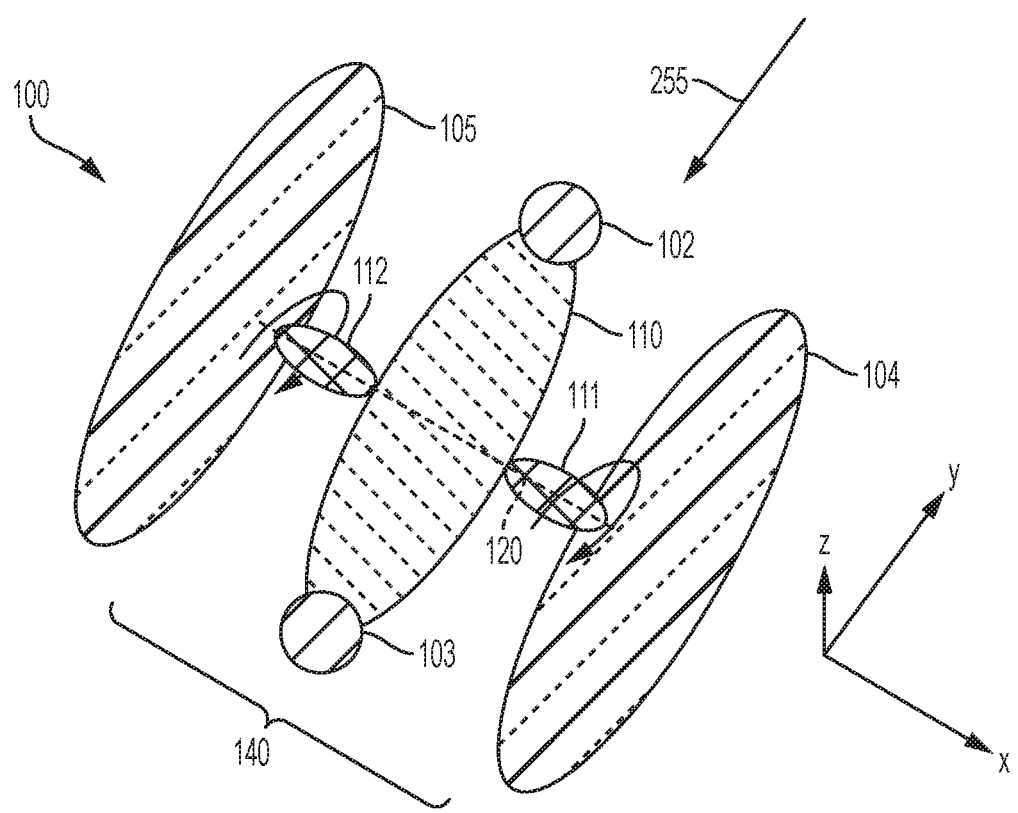

FIG. 2 illustrates the tunable electromagnetic response of the reconfigurable polar molecule 100. In the coordinate system shown, primary rotating element 140 lies in the x-y plane between first support 104 and second support 105, and the z-axis points into the page. The axis of rotation 120 is located along the x-axis.

Upon application of an external electric field 255, primary rotating element 140 rotates along its axis of rotation 120, away from the x-y plane and into the z-plane by a rotation angle θ. Although the electric field 255 is shown as being applied in the y-axis direction, the electric field 255 may be applied in any direction(s). The magnitude of the applied electric field 255 determines the amount of rotation and the rotation angle θ. The permanent dipole across the elongated segment 110 due to the first charged end 102 and second charged end 103 induces the rotation. Because primary rotating element 140 is rigid, it remains anchored in first support 104 and second support 105 during rotation. Also because first bridging group 111 and second bridging group 112 are linear groups, allow free rotation towards the z-plane, which is arranged substantially perpendicular to the x-y plane.

As the primary rotating element 140 rotates through rotation angle θ, a number of stable and unstable conformations may be possible. Some conformations may be more energetically favored than others. The stability of the conformations depends on the composition of the primary rotating element 140 and the surrounding packaging 304 (including first support and second support). Upon application of the electric field 255, primary rotating element 140 rotates through rotation angle θ to the lowest energy conformation.

The above-described reconfigurable polar molecules may be combined into a plurality and ordered or arranged in a lattice to form a solid state material. Compared to liquid crystalline materials, the solid state materials have improved thermal stability and therefore may be used in wider temperature ranges. For example, the reconfigurable polar molecules and solid state materials made therefrom may be used at temperatures in a range from cryogenic to about 400° C., or possibly higher depending on the package thermal insulation or host matrix.

The reconfigurable polar molecules described above also provide other advantages. The molecules can be used as a dopant for a host material. For example, if polar molecules are in a dielectric material, under certain conditions, they may be aligned and become radiators (antenna/dipoles). In another example, the polar molecule adaptive orientation will impact the reflectivity/transmissivity of the material.

The polar molecules and materials may be used in RF and IR optical applications. The molecules and materials also can be applied in the fields of spintronic devices and logic gates. The molecules and materials also can interact with incoming signals of various polarizations, functioning as a sensor. Further, the molecules and materials may be used as a polarization transformer. Because of their size, the molecules can be used to implement switching capability down to the nanometer scale.

The shape of the support structure/packaging (first support 104 and second support 105) governs three-dimensional assembly of the reconfigurable polar molecule 100 into the lattice of the solid state material.

Figure 3:
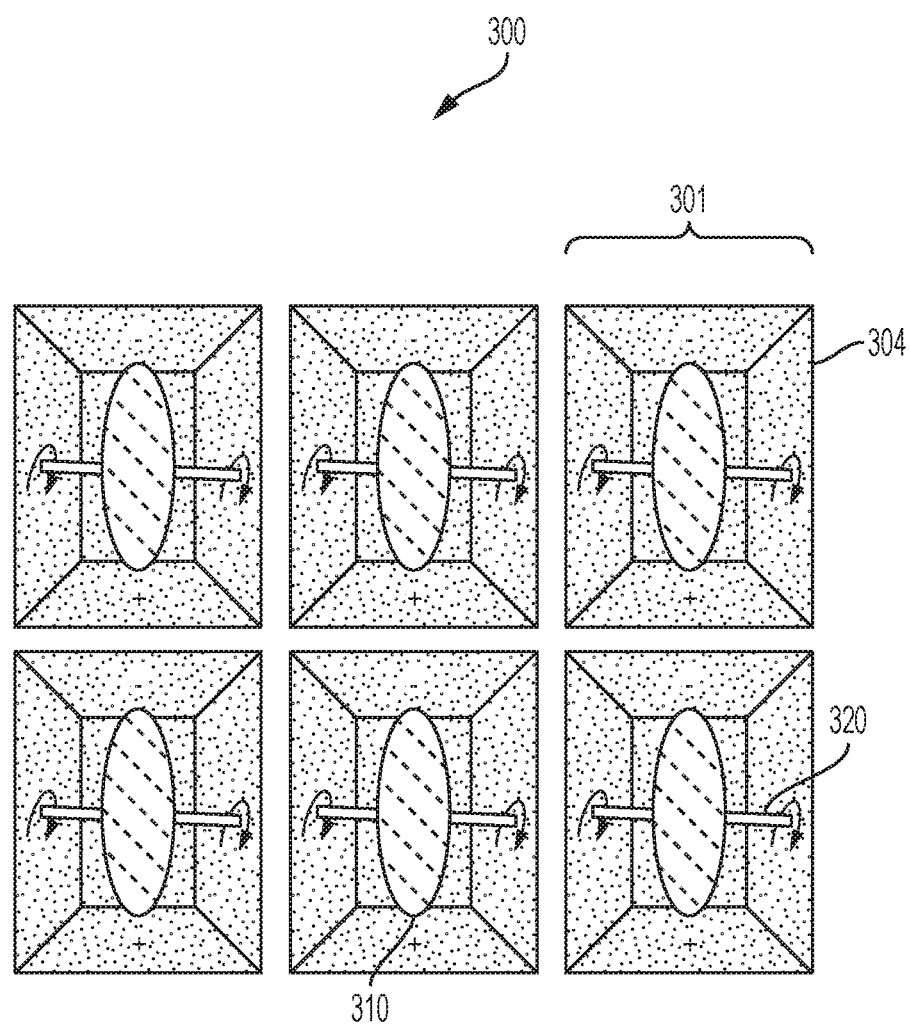

In an exemplary embodiment, FIG. 3 illustrates a solid state material 300 having unit cells 301 of reconfigurable polar molecules arranged in a lattice. Each of the unit cells 301 include a primary rotating element that includes an elongated segment that includes a first charged end with a positive charge and a second charged end with a negative charge. The primary rotating element is a rigid molecule with a permanent dipole. The primary rotating element has an axis of rotation 320 that extends through its center of mass. The primary rotating element is anchored by bridging groups (first bridging group and second bridging group) (not shown in FIG. 3 for clarity) in a packaging 304 (including a first support and second support). The packaging 304 provides a housing around the rotational path of the primary rotating element to insulate from dispersion and ambient vibrational modes.

Figure 4A:
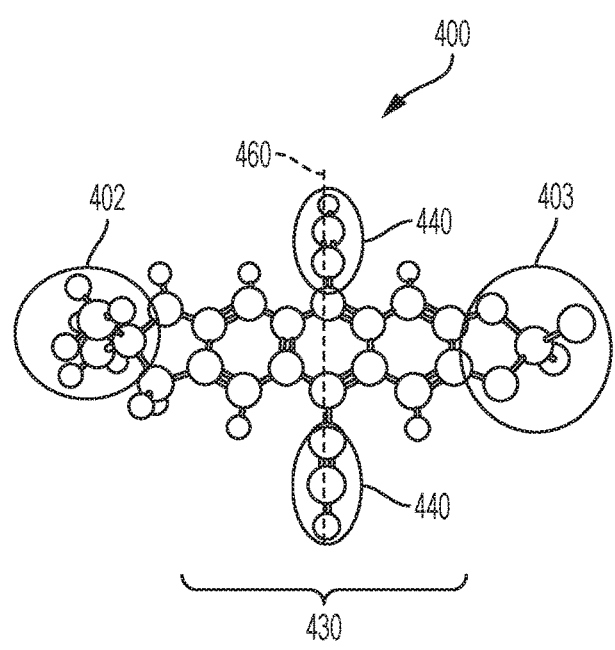
FIG. 4A is a three-dimensional illustration of a primary rotating element of a reconfigurable polar molecule.

FIG. 4A is a three-dimensional illustration of primary rotating element 400 according to an embodiment. The primary rotating element 400 is an ammonium phosphate ethynyl-anthracene derivative, which has the following chemical structure:

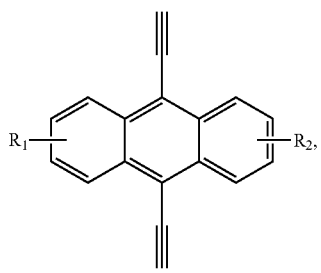

wherein $R_1$ is an ammonium group ($-N(R)_3^+$), and $R_2$ is a phosphate group ($PO_4(R)_2^-$).

Figure 4B:
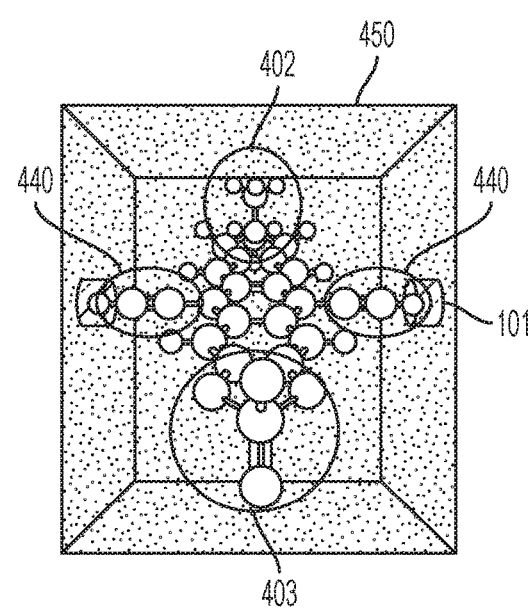

An ethynyl-anthracene molecule forms elongated segment 430. The ethynl groups arranged on opposing sides of the central ring portion of the anthracene form the bridging groups 440 (first bridging group and second bridging group) that will anchor the primary rotating element 400 to the packaging 450, as shown in FIG. 4B. The axis of rotation 460 extends through the bridging groups 440.

The ethynyl-anthracene molecule is derivatized with a positively charged ammonium group to form first charged end 402. The ethynyl-anthracene derivative is derivatized with a negatively charged phosphate group to form second charged end 403. However, the derivatives on the ethynyl-anthracene molecule portion may be optimized for specific applications.

FIG. 4B is an illustration of the primary rotating element 400 anchored within a packaging 450 architecture. The packaging 450 (or support) include polyaromatic walls that minimize dispersion during rotation of the primary rotating element 400. The ammonium group and the phosphate group provide a permanent dipole across the primary rotating element 400, which is oriented through an applied electric field. The ethynyl groups forming the bridging groups 440 that anchor the primary rotating element 400 on the axis of rotation 460 that provides a low barrier to rotation.

It is noted that FIG. 4B is shown for illustrative purposes only. Although the ethynyl groups of primary rotating element 430 are shown as being superimposed into packaging 450, the ethynyl groups will form covalent bonds (carbon-carbon bonds) with the molecule of the packaging 450. For example, the reaction between the primary rotating element 400 and packaging 450 is illustrated by the following reaction scheme:

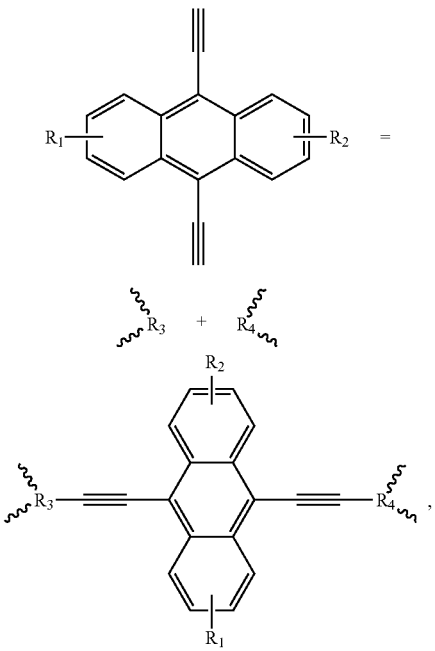

Where in $R_1$ is an ammonium group, $R_2$ is a phosphate group, $R_3$ is a carbon-containing group of first support, $R_4$ is a carbon-containing group of second support, and covalent carbon-carbon bonds are formed between the ethynyl groups and each of $R_3$ and $R_4$.

The reconfigurable polar molecules described in the above embodiments may be used in a variety of applications, for example, as sensors or molecular switches. When used as a switch, the molecules are switched between "on" and "off" states. The reconfigurable polar molecule may be placed between two electrodes so that an electric field with an appropriate magnitude and orientation, produced between the two electrodes, causes the primary rotating element to rotate. The orientation of the molecule located between the two electrodes can vary depending on the type of molecule selected and how the molecule is used.

When the reconfigurable polar molecules, and solid state materials made therefrom, are used as a sensor, the molecules can interact with incoming signals (electric fields) of various polarizations. For example, in one case, when the polar molecules aligned together to the direction of the incident field, they may act as an array of infinitesimal dipoles (nanometer scale), which is equivalent of an antenna structure. In another example, the polar molecule can act as a polarization filter to filter out undesirables frequencies based on polarization.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A reconfigurable polar molecule, comprising:
a symmetric nonpolar molecule portion having an elongated shape and defined by a longitudinal axis and a lateral axis, the longitudinal axis being longer than the lateral axis;
a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule;
a first bridging group and a second bridging group arranged on the lateral axis of the symmetric nonpolar molecule on opposing sides, the first bridging group and the second bridging group being linear nonpolar groups; and
a first support portion bonded to the first bridging group, and a second support portion bonded to the second bridging group, the first bridging group and the second bridging group being nonpolar and having structures that enable free rotation of the symmetric nonpolar molecule portion through the first bridging group and the second bridging group;
wherein the reconfigurable polar molecule has the following structure:

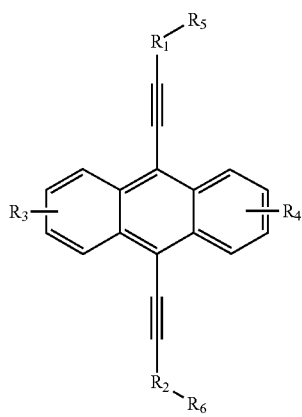

wherein $R_1$ and $R_2$ are each independently a single bond, a $C_2$-$C_4$ alkyl group, a $C_2$-$C_4$ alkenyl group, a $C_2$-$C_4$ alkynyl group, or any combination thereof; $R_3$ is the positive ionically charged group; $R_4$ is the negative ionically charged group; $R_5$ is the first nonpolar support portion; and $R_6$ is the second nonpolar support portion.

2. A solid state material comprising a plurality of the reconfigurable polar molecules of claim 1, wherein the plurality of the reconfigurable polar molecules are ordered in a lattice.

3. A reconfigurable polar molecule, comprising:
a symmetric nonpolar molecule portion having an elongated shape, comprising a polyaromatic ring structure, and defined by a longitudinal axis and a lateral axis, the longitudinal axis being longer than the lateral axis;
a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule;
a first bridging group and a second bridging group arranged on the lateral axis of the symmetric nonpolar molecule on opposing sides, the first bridging group and the second bridging group being linear nonpolar groups;
an axis of rotation extending from the first bridging group to the second bridging group along the lateral axis of the symmetric nonpolar molecule; and
a first nonpolar support portion bonded to the first bridging group on one side of the symmetric nonpolar molecule, and a second nonpolar support portion bonded to the second bridging group on an opposing side of the symmetric nonpolar molecule, the first bridging group and the second bridging group being nonpolar and having structures that enable free rotation of the symmetric nonpolar molecule portion through the first bridging group and the second bridging group;
wherein the reconfigurable polar molecule has the following structure:

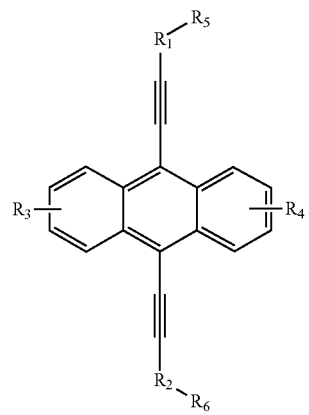

wherein $R_1$ and $R_2$ are each independently a single bond, a $C_2$-$C_4$ alkyl group, a $C_2$-$C_4$ alkenyl group, a $C_2$-$C_4$ alkynyl group, or any combination thereof; $R_3$ is the positive ionically charged group; $R_4$ is the negative ionically charged group; $R_5$ is the first nonpolar support portion; and $R_6$ is the second nonpolar support portion.

4. The reconfigurable polar molecule of claim 3, wherein the first nonpolar support portion and the second nonpolar support portion each comprise a polyaromatic molecule.

5. The reconfigurable polar molecule of claim 3, wherein the first nonpolar support portion is covalently bonded to the first bridging group, and the second nonpolar support portion is covalently bonded to the second bridging group.

6. The reconfigurable polar molecule of claim 3, wherein the positive ionically charged group is an amine group, an ammonium group, a phosphonium group, a sulfonium group, salts thereof, or any combination thereof; and the negative ionically charged group is a carboxylate group, a phosphate group, a phosphonate group, a sulfate group, a sulfonate group, a nitrate group, a nitrite group, a tosylate group, a brosylate group, a mesylate group, a selenate group, salts thereof, or any combination thereof.

7. A solid state material comprising a plurality of the reconfigurable polar molecules of claim 3, wherein the plurality of the reconfigurable polar molecules are ordered in a lattice.

8. A method of using a reconfigurable polar molecule, the method comprising:

forming the reconfigurable polar molecule, comprising:
a symmetric nonpolar molecule portion having an elongated shape and defined by a longitudinal axis and a lateral axis, the longitudinal axis being longer than the lateral axis;

a positive ionically charged group arranged on the longitudinal axis of the symmetric nonpolar molecule at a first end and a negative ionically charged group arranged on the longitudinal axis of the symmetric nonpolar molecule at a second end, the positive ionically charged group and the negative ionically charged group forming a permanent dipole through the longitudinal axis of the symmetric nonpolar molecule;

a first bridging group and a second bridging group arranged on the lateral axis of the symmetric nonpolar molecule at opposing sides, the first bridging group and the second bridging group being linear nonpolar groups; and a first support portion bonded to the first bridging group, and a second support portion bonded to the second bridging group, the first bridging group and the second bridging group being nonpolar and having structures that enable free rotation of the symmetric nonpolar molecule portion through the first bridging group and the second bridging group with respect to the first support portion and the second support portion;

wherein the reconfigurable polar molecule has the following structure:

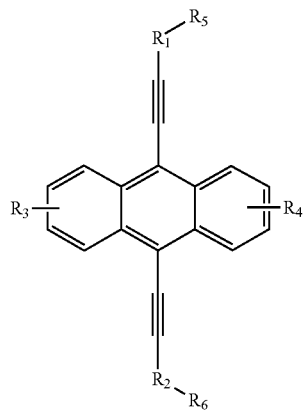

wherein $R_1$ and $R_2$ are each independently a single bond, a $C_2$-$C_4$ alkyl group, a $C_2$-$C_4$ alkenyl group, a $C_2$-$C_4$ alkynyl group, a cyano group, or any combination thereof; $R_3$ is the positive ionically charged group; $R_4$ is the negative ionically charged group; $R_5$ is the first nonpolar support portion; and $R_6$ is the second nonpolar support portion; and applying an electric field to the reconfigurable polar molecule to induce the reconfigurable polar molecule to rotate through an axis of rotation that extends through the lateral axis of the symmetric nonpolar support molecule.

9. The method of claim 8, wherein the reconfigurable polar molecule is initially arranged in an x-y plane, and applying the electric field induces the reconfigurable polar molecule to rotate away from the x-y plane and towards a z-plane that is arranged perpendicular to the x-y plane.

10. The method of claim 8, wherein the reconfigurable polar molecule is arranged in a solid state material.

11. The method of claim 8, wherein the reconfigurable polar molecule rotates in response to applying the electric field at a temperature in a range from about cryogenic to about 400° C.

12. The method of claim 8, wherein the first support portion and the second support portion comprise a polyaromatic ring structure.

* * * * *